United States Patent [19]
Berg et al.

[11] Patent Number: 5,888,248
[45] Date of Patent: Mar. 30, 1999

[54] DERMAL-EPIDERMAL IN VITRO TEST SYSTEM

[76] Inventors: Richard A. Berg, 1729 Linvale Harbourton Rd., Lambertville, N.J. 08530-3302; Jeffrey Geesin, 34 Eaton Ct., Newton, Pa. 18940

[21] Appl. No.: 477,796

[22] Filed: Jun. 7, 1995

Related U.S. Application Data

[63] Continuation of Ser. No. 352,979, Dec. 9, 1994, abandoned, which is a continuation of Ser. No. 32,373, Mar. 17, 1993, abandoned.

[51] Int. Cl.$^6$ .............................. A61F 2/00; A61K 35/12
[52] U.S. Cl. ........................... 623/66; 435/240.1; 623/15
[58] Field of Search ................................ 623/1, 2, 10, 11, 623/12, 66; 435/31–33, 5–6, 240.1, 240.2, 240.23, 240.24, 240.241; 436/5

[56] References Cited

U.S. PATENT DOCUMENTS

| | | | |
|---|---|---|---|
| 4,485,096 | 11/1984 | Bell | 424/95 |
| 4,604,346 | 8/1986 | Bell et al. | 435/1 |
| 4,703,108 | 10/1987 | Silver et al. | 530/356 |
| 4,835,102 | 5/1989 | Bell et al. | 435/29 |
| 4,837,285 | 6/1989 | Berg et al. | 530/356 |
| 4,837,379 | 6/1989 | Weinberg | 424/101 |
| 4,841,962 | 6/1989 | Berg et al. | 128/156 |
| 4,925,924 | 5/1990 | Silver et al. | 530/356 |
| 4,963,489 | 10/1990 | Naughton et al. | 435/240.1 |
| 4,970,298 | 11/1990 | Silver et al. | 530/356 |
| 5,032,508 | 7/1991 | Naughton et al. | 435/32 |
| 5,106,949 | 4/1992 | Kemp et al. | 530/356 |
| 5,273,900 | 12/1993 | Boyce | 435/240.23 |
| 5,282,859 | 2/1994 | Eisenberg | 623/11 |

FOREIGN PATENT DOCUMENTS

| | | |
|---|---|---|
| 0 361 957 A1 | 4/1990 | European Pat. Off. . |
| 0 403 139 A1 | 12/1990 | European Pat. Off. . |
| 0 418 035 A1 | 3/1991 | European Pat. Off. . |
| WO 80/01350 | 7/1980 | WIPO . |

OTHER PUBLICATIONS

Dykes, In Vitro Reconstruction of Human Skin: The Use Of Skin Equivalents as Potential Indicators
Dykes, TJ. "In Vitro Reconstruction of Human Skin; The use of Skin Equivalents as Potential Indicators of Cut Angus Toxicity" Toxic. in Vitro vols pp. 1–7, 1991.
Leighton, J. et al. Patterns of 3–D Growth in Vitro in Collagen–Coated Cellulose Sponge: Carcinomas and Embroyonic Tissues Cancer Research 28, 286–286. 1968.
Bell et al., "The Reconstitution of Living Skin", *Journal of Investigative Dermatology* 1983, 81, 2s–10s.
Doilllon et al., "Behavior of Fibroblasts and Epidermal Cells Cultivated on Analogues of Extracellular Matrix", *Biomaterials* 1988, 9, 91–96.

*Primary Examiner*—Davidd Isabella
*Attorney, Agent, or Firm*—Woodcock Washburn Kurtz Mackiewicz & Norris, LLP

[57] ABSTRACT

This invention relates to a skin model system that can be used as an in vitro test system or which can be used for therapeutic purposes. The skin model system comprises a three-dimensional, cross-linked matrix of insoluble collagen containing fibroblast cells therein, and stratified layers of differentiated epidermal cells supported thereon.

12 Claims, 6 Drawing Sheets

DERMAL-EPIDERMAL IN VITRO TEST SYSTEM

This a continuation, of application Ser. No. 08/352,979, filed Dec. 9, 1994, now abandoned, which in turn is a continuation of Ser. No. 08/032,373, filed Mar. 17, 1993, now abandoned.

FIELD OF THE INVENTION

This invention relates to artificial skin, its preparation, and its use.

BACKGROUND OF THE INVENTION

For some time, there has been a move to develop an artificial skin that can be used (1) for wound healing and the repair of ulcerated, burned or lacerated skin, and (2) as a model to test substances for irritation, toxicity, inflammation and pharmacology so as to reduce the number of tests using live animals. This latter application for artificial skin is commonly referred to as an in vitro alternative to animal testing.

Berg and colleagues (U.S. Pat. Nos. 4,703,108 and 4,970,298, the disclosures of which are herein incorporated by reference) have developed a biocompatible, chemically crosslinked, three-dimensional collagen matrix as a substitute for the dermal layer of the skin where it promotes fibroblast ingrowth and proliferation when implanted into animals (Doillon, et al., "Fibroblast-collagen sponge interactions and the spatial deposition of newly synthesized collagen fibers in vitro and in vivo," *J. Scanning Electron Microscopy*, III:1313–1320 (1984). It has also been used to treat human Decubitus ulcers where it promotes healing (Silver, F. H., et al., "Collagenous materials enhance healing of chronic skin ulcers," *Biomedical Materials and Devices Research Society*, 110:371–376 (1989)). In vitro studies, this matrix has been used as a model for examining the role of various matrix components on fibroblast ingrowth (Doillion, et al., "Fibroblast growth on a porous collagen sponge containing hyaluronic acid and fibronectin," *Biomaterials* 8:195–200 (1987).

In this invention, this matrix is used as a support for human keratinocyte growth and differentiation. The matrix described herein, containing keratinocytes and fibroblasts, is referred to herein as a "skin model system" or "SMS." Dollion, et al., in "Behavior of fibroblasts and epidermal cells cultivated on analogues of extracellular matrix," *Biomaterials*, 9:91–96 (1988), report on efforts to use the Berg collagen matrix in attempts to manufacture artificial skin, but such attempts were not successful. Epidermal cells on the surface of the matrix were neither differentiated nor in stratified layers.

An alternative collagen-based system has been developed by Bell et al. (Bell, E., et al., "The reconstitution of living skin," *Journal of Investigative Dermatology*, 81:2s–10s (1983); Bell, E., et al., "Recipes for reconstituting skin," *J. Biomechan. Eng.*, 113:113–119 (1991)) as a dermal replacement called "living skin equivalent" or "LSE". The LSE is manufactured by mixing living human fibroblasts with soluble rat tail collagen under conditions where the collagen forms a gel (See, U.S. Pat. Nos. 4,485,096, 4,604,346, 4,8356,102, and Bell, E., et al., "Production of a tissue-like structure by contraction of collagen lattices by human fibroblasts of different proliferative potential in vitro," *Proc. Natl. Acad. Sci. USA*, 76:1274–1278 (1979)). During the five days of culture, the gel containing fibroblasts undergoes a contraction process where the collagen volume is reduced to a small disc approximately 10% to 20% of the original volume depending on the concentration of collagen, the cell number and the composition of the growth medium. This contracted collagen matrix is then used to support human keratinocyte growth. Although the Bell LSE is an advance over other previously known artificial skin systems, it does suffer from disadvantages. Since the manufacture or the collagen matrix requires living fibroblasts, it is expensive to manufacture and the matrix is not easily stored. The Bell collagen matrix is not cross-linked and contracts with the addition of the fibroblasts, so it is difficult to manufacture the matrix in a desired shape and size. It is difficult to make large sizes of LSE; the matrix contracts substantially and large numbers of living cells are required. The Bell collagen matrix utilizes soluble collagen, which is more difficult and expensive to extract than insoluble collagen. Still further, since the Bell collagen matrix requires living cells, the manipulations to which it can be exposed are limited, e.g., it cannot be exposed to toxic conditions which might manipulate or favorably alter the matrix structure but which would kill the cells. In view of cheese limitations, there remains a need for improved artificial skin systems.

SUMMARY OF THE INVENTION

It has now been found that a cross-linked matrix of insoluble collagen can be used as the matrix for preparing a skin model system mimicking human skin. This invention relates to such a skin model system, comprising a three-dimensional, cross-linked matrix of insoluble collagen containing fibroblast cells therein, and stratified layers of differentiated epidermal cells supported thereon.

This invention further relates to a method for preparing such a skin model system comprising (a) providing a three-dimensional, cross-linked collagen matrix, (b) seeding said matrix with fibroblasts and culturing the seeded matrix under conditions to allow ingrowth and proliferation of said fibroblasts, (c) seeding the surface of said matrix with epidermal cells in a manner to deter ingrowth of said epidermal cells, (d) culturing the seeded matrix for a first period of time under conditions to allow said epidermal cells to attach to said matrix and proliferate to form a monolayer and (e) culturing the seeded matrix for a second period of time under conditions to allow said epidermal cells to differentiate.

Still further, this invention relates to methods for using the skin model system of this invention to determine the effect of an agent on human skin comprising contacting the skin model system with said agent and measuring the interaction of the skin model system and said agent.

Still further, this invention relates to methods for using the skin model system of this invention to treat wounds comprising transplanting said skin model system as a graft at the wound.

BRIEF DESCRIPTION OF THE DRAWINGS

FIGS. 6 are photomicrographs of cross-sections of human foreskin or of epidermal cell cultures grown on a collagen matrix. Magnification is 400×, except were noted.

DETAILED DESCRIPTION OF THE INVENTION

Figure 1:
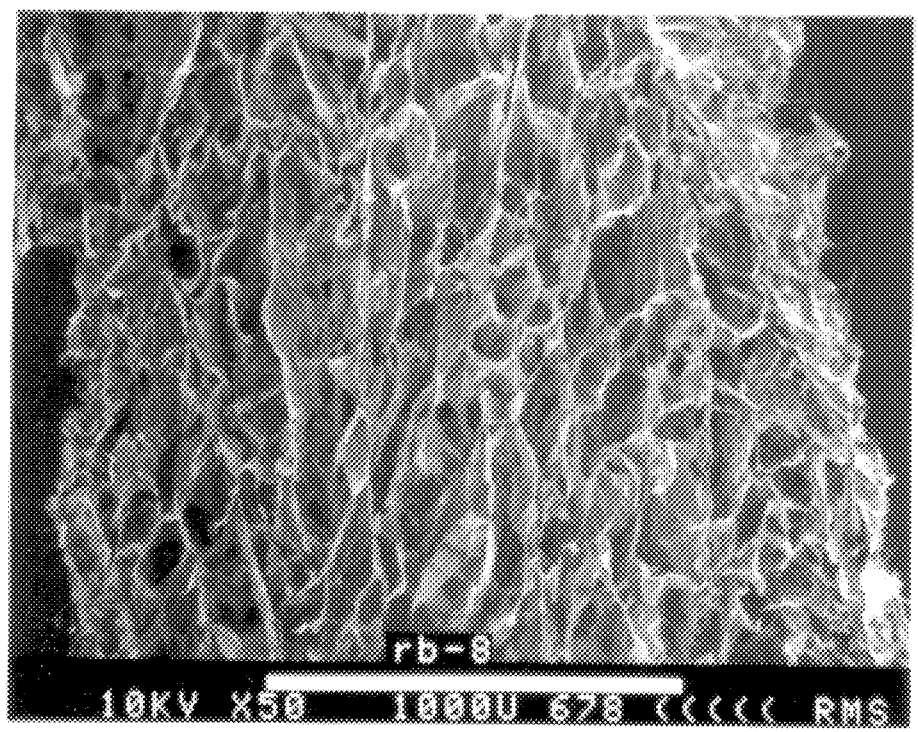
FIG. 1 is a scanning electron micrograph (SEM, of a cross-section of unmodified, cross-linked collagen matrix of insoluble collagen. A $1000\mu$ bar is shown.

Skin is composed of both a dermal layer, consisting primarily of types I and III collagen, proteoglycans, elastin and other matrix macromolecules, and epidermal layers, consisting of epidermal cells containing keratin filaments undergoing progressive differentiation from a basal proliferating layer to a surface consisting of terminally differentiated, epidermal cells that protect the skin from the environment. The skin model system of this invention mimics the composition of normal skin. Fibroblast cells are grown within a three-dimensional matrix formed of cross-linked, insoluble collagen to form a dermal-type layer which supports stratified layers of differentiated epidermal cells.

The collagen matrix utilized in this invention is based on insoluble collagen. "Insoluble collagen" refers to collagen which cannot be dissolved in aqueous acidic or alkaline or in any inorganic salt solution without chemical modification. Preferred sources of the insoluble collagen include hides, splits and other mammalian or reptilian coverings. More preferably, the collagen is derived from the corium, the intermediate layer of a bovine hide between the grain and flesh sides. More generally, however, the collagen can be derived from the following typical sources: type I collagen: bovine, chicken and fish skin, bovine and chicken tendons and bovine and chicken bones including fetal tissues; type II collagens: bovine articular cartilage, nasal septum, sternal cartilage; and type III collagen, bovine and human aorta and skin.

The insoluble collagen is dispersed and swollen in a suitable liquid media, such as dilute hydrochloric acid, acetic acid or the like, having a Ph between about 3.0 and 4.0. Generally, a weight ratio of insoluble collagen to dispersion agent of from about 1 to 15 is used to form the dispersion. This dispersion is poured into molds (generally, plastic or metal trays) of the desired shape and size. For skin model systems, it is generally preferred that the thickness of the matrix be within about 1 to 5 mm, preferably about 2–3 mm, so the size and shape of the mold can be determined accordingly. The dispersion is solidified by freezing and is then lyophilized to form a three-dimensional, porous matrix.

Prior work has demonstrated that the pore size of the matrix is important to achieve optimal cell ingrowth. See U.S. Pat. No. 4,970,298, the disclosure of which is herein incorporated by reference. Generally, a matrix having a pore size of 50 to 250 microns, preferably in the range of 100±50 microns, containing channels is an ideal structure for a collagen-based material for cell ingrowth. (Pore size may be measured from a photomicrograph using a ruler, averaging two measurements of a pore taken at 90° angles from one another, and averaging such measurements over a representative number of pores.) The optimum conditions for forming a matrix having these characteristics are: (1) to avoid excessive blending and obtain a well dispersed mixture of large collagen fibers, (2) to disperse the collagen in a liquid media having a Ph of about 3.0 to about 4.0, (3) to freeze the collagen dispersion to from about −30° C. to about −50° C. in an ethanol bath, and (4) to keep the ethanol bath in direct contact with the plastic or metal tray to avoid any air gap. After freezing, lyophilization is generally carried out under conditions of a sample temperature of about 0° to 20° C. and a vacuum below about 200 mTorr Hg.

As noted in U.S. Pat. No. 4,970,298, the upper surface of the sponge in direct contact with the atmosphere during the freeze-drying process, called the "air side", is found to have a collapsed form or a sheet-like structure in almost all cases. The other side of the sponge, in direct contact with the tray, called the "pan side", is found to have a more open, delicate structure. The average pore size on the pan side tends to be significantly smaller (e.g., generally at least about 100μ smaller) than that of the air side. Not reported in U.S. Pat. No. 4,970,298, but described hereinbelow, is the importance of seeding the epidermal cells on the "pan side" of the sponge rather than the "air side" to achieve the optimal skin model system.

Prior to solidifying the collagen dispersion other agents may be incorporated into the dispersion. For example, polycationic polymers such as polylysine or polyaspartic acid may be incorporated to improve cell growth. Carrier compounds such as collagen types IV and V, fibronectin, laminin, hyaluronic acid, proteoglycans, epidermal growth factor, platelet derived growth factor, angiogenesis factor, antibiotic, antifungal agent, spermicidal agent, hormone, enzyme and enzyme inhibitor.

Following lyophilization, the collagen matrix is cross-linked. Preferably, cross-linking is carried out by a dehydrothermal treatment. Suitable conditions include subjecting the matrix to temperatures of from about 50° C. to about 200° C. at a vacuum of 50 millitorr or less for a period of time from about 2 to 96 hours. However, the collagen may also be cross-linked by chemical agents (or a combination of dehydrothermal treatment and chemical agents) such as carbodiimide or succinimydyl ester/carbodiimide.

Examples of the carbodiimides include cyanamid and 1-ethyl-3-(3-dimethylaminopropyl)-carbodiimide hydrochloride. Examples of bifunctional succinimidyl active esters include bifunctional N-hydroxysuccinimide, 3,3'-dithio(sulfosuccin-imidyl)proprionate and bis(sulfosuccinimidyl)suberate. When using a carbodiimide cross-linking agent, the collagen-based matrix is immersed in a carbodiimide solution at a concentration of from about 0.1 to 10% (W.V) maintained at a temperature of from about 2° C. to 40° C. and at a Ph of between 2 to 11 for a period of time of from about 2 to 96 hours. When using a succinimidyl active ester crosslinking agent, the collagen-based sponge or sheet is immersed in a solution thereof at a concentration of from about 0.1 to about 15.0% (W/V) maintained at a temperature of from about 2° C. to 40° C. for a period of time of from about 2 to 96 hours. The collagen-based sheet is placed in a solution containing 0.1 to about 15% (W/V) of N-hydroxysuccinimide and carbodiimide at a Ph between 2 to 11 for a period of time between 2 to 96 hours at a temperature of from about 2° C. to 40° C. The thus-treated intermediate collagen-based matrix is exhaustively washed to remove excess cross-linking agent.

Unlike prior art collagen matrices prepared from collagen and living cells, the collagen matrices of this invention can be stored for periods of time in a dry state. For example, experience has suggested that sterilized matrices can be stored under dry and sealed conditions in excess of two years. Prior to storage or use, it is generally preferred to sterilize the matrices, e.g., with gamma irradiation. Prior to seeding the matrices with living cells, the matrices are preferably treated (e.g., soaked overnight in DMEM supplemented with 10% calf serum to remove any residual acid.

The next step in preparing the skin model system described herein is seeding the collagen matrix with fibroblasts. Fibroblasts will be dispersed throughout the collagen matrix to simulate the dermal layer of humans and other mammals. Although the type of fibroblast utilized is not critical, it is preferred to use dermal fibroblasts as they will deposit the appropriate types of collagen and other dermal components. The fibroblasts may be of human or animal origin. They may be commercially obtained or may be cultured from a patient biopsy. Fibroblast-like cells may also be used. Other cells may also be cultured in the collagen matrix, including but not limited to endothelial cells, pericytes, macrophages, monocytes, lymphocytes, plasma cells and adipocytes.

The fibroblasts are generally inoculated onto the matrix at a density of about 0.2 to $1 \times 10^6$ cells per 2×2 centimeter of matrix. Preferably, the fibroblasts are inoculated onto the "air side" of the matrix as the greater pore size on this side encourage ingrowth of the fibroblasts into the matrix. However, it should also be possible to seed the "pan side" of the matrix. As mentioned above, pore sizes in the range of about 100±50μ have been found to be ideal for cell ingrowth. The seeded matrix is cultured for a period of time and under conditions to allow the cells to grow and modify the collagen matrix so that it will support the growth of epidermal cells. During this period, the fibroblasts substantially fill the spaces in the collagen matrix, generally, a period of from about one to fifteen days, preferably about five days. Suitable culture conditions would be known to those skilled in the art and would be conditions conducive to the proliferation of the fibroblasts. Such conditions include immersing the seeded matrix in DMEM (Dulbeco's Modified Eagle's Medium) supplemented with 5% FBS (fetal bovine serum) or 10% bovine serum for five to seven days.

The next step involves seeding the matrix with epidermal cells. These epidermal cells must be keratinocytes, although other cells may be used in conjunction with the keratinocytes (e.g., melanocytes). Epidermal cells are generally inoculated onto the matrix at a density of about 100,000 to about 500,000 cells per cm$^2$, although lesser or greater amounts could be used. The epidermal cells must be seeded onto the "pan side" of the matrix. It has been found that if the cells are seeded onto the "air side", with its open, large pore structure, the cells migrate into the matrix to produce swirls and pockets of epidermal cells. Applying epidermal cells to the pan side, that side with the smallest pore structure, improved epidermal cell growth and proliferation by minimizing ingrowth of the epidermal cells into the matrix.

The matrix seeded with epidermal cells is cultured for a first period of time and under conditions suitable to allow the epidermal cells to attach and form a monolayer. Generally, this may be accomplished by submerging the seeded matrix in an epidermal growth media for approximately one week at 37° C. and 7% $CO_2$. A suitable epidermal growth media ("E-media") contains: 3:1 high glucose DMEM supplemented with Ham's F-12 Nutrient Mixture (Gibco), $5 \times 10^{-10}$M cholera toxin (Schwarz-Mann Biotech), 2 μg/ml hydrocortisone, 25 μg/ml insulin, 25 μg/ml transferrin, and $1 \times 10^{-10}$M triiodothyronine (all from Sigma Chemical Company).

Once the epidermal cells have proliferated to form a monolayer, the matrix is cultured for a second period of time under conditions to allow the epidermal cells to differentiate. The culture or matrix is raised so that the surface seeded with epidermal cells is exposed to the atmosphere, e.g., by raising the matrix to the liquid/air interface in the culture. The matrix continues to be fed with the epidermal growth media and held until the epidermal cells have differentiated as desired. A period of twenty-one days has been found to be sufficient, although shorter or longer periods may be utilized.

Tests indicate that the epidermal cells grown on the collagen matrix as described above form stratified layers similar to skin with the epidermal cells differentiating as they approach the surface. Those skilled in the art would know how to determine whether a stratified layer of cells is present. Stratified layers of epidermal cells are found where several layers of cells are piled on top of one another as opposed to being in a single monolayer (or to simply filling in holes in the collagen matrix). Generally, the stratified layers formed in this invention will comprise a layer of three or more, preferably five or more, cell thicknesses.

Those skilled in the art would also know how to determine whether epidermal cells have differentiated. Cells that have differentiated show a change in morphology (shape and appearance) and often secrete certain proteins. Changes in morphology include (1) the presence of granules in the granular layer (or a layer in the SMS approximating the granular layer), (2) the flattening of the cells and (3) the loss of cell nuclei. The presence of any one or more of these changes in morphology indicates that the cells have differentiated or are differentiating.

When epidermal cells differentiate, they also start to make certain proteins. For the purpose of this invention, the presence of any one or more of those proteins in the epidermal cells is evidence that the cells have differentiated or are differentiating. Those proteins include involucrin, filaggrin, keratin K1 and loricrin.

Involucrin is a cell envelope protein present in all but the basal layers of normal skin and is one of the earlier proteins produced for the formation of the corneocyte envelope in human skin. The corneocyte envelope is a rigid alkaline-resistant structure produced only by differentiating keratinocytes and not by basal keratinocytes.

Filaggrin is a protein produced in the suprabasal layer as profilaggrin which is processed to filaggrin. In human skin, it is found in the upper stratum spinosum and granulosum. Filaggrin is generally not found in the stratum corneum, possibly because it is degraded to amino acids in that layer. Filaggrin is involved in the preparation of keratohyalin granules formed in differentiating cells of the epidermis. Only differentiating cells would produce filaggrin.

Keratins are a family of proteins whose members are expressed as a function of the differentiation state of the epidermal cells. The keratin K1 (having a molecular weight of 67 kDa), is the keratin present in the most highly differentiated keratinocytes. In normal skin, K1 is localized to the upper stratum spinosum and granular layers.

Loricrin is a major cornified envelope precursor, which is one of the latest envelope proteins to be expressed in normal skin. When using an antibody specific to the epitopes on the N-terminal portion of loricrin, normal foreskin has been found to stain specifically from the upper stratum spinosum to the stratum corneum.

The presence of these proteins in the skin model system can be determined by standard immunohistochemical techniques described in more detail in the Examples. Tests show that the amounts and distribution of each of these proteins in the skin model system of this invention mimic their distribution in normal neonatal skin. The only exception to this pattern was that reduced amounts of loricrin were determined in the skin model system matrix described herein compared to normal skin.

The skin model system described herein should have a variety of uses. Chemicals such as drugs, cosmetics, pesticides and food additives must often be tested for skin irritation, for toxicity and/or for efficacy. Currently, much of this testing is carried out on laboratory animals. The skin model system of this invention, however, closely resembles human skin and can be used not only to spare laboratory animals but also to more accurately gauge the effect of a chemical on human skin. One aspect of this invention, therefore, relates to a method of determining the effect of a chemical or other agent on human skin comprising contacting a skin model system of this invention with said chemical or agent and measuring the interaction of the skin model system and said chemical or agent. The term "agent" is intended to encompass not only substances but conditions such as light, heat, etc. Such interactions could include, but are not limited to, the release of one or more substances by the skin model system, an effect on metabolism or cell proliferation or differentiation of the cells, or the reorganization of the cells of the system. The extent to which the chemical or agent is likely to affect human skin is determined by the extent of any such interaction with the skin model system. In this way, the potential toxicity or potential for irritation of a chemical or other agent may be determined, as may the potential pharmacological efficacy of a chemical or other agent be determined.

Other utilities for the skin model system of this invention include its use as a model for studying skin diseases and developing new treatments for skin ailments. For example, one could form the skin model system of this invention using cell lines from patients with a certain disease to learn more about that disease and to study and evaluate the efficacy of treatments for it. More specifically, one aspect of this invention relates to a method for determining the efficacy of a treatment for a skin condition comprising (a) providing the skin model system of this invention wherein diseased cells typical of said condition have been used to produce said system, (b) exposing said skin model system to said treatment, and (c) monitoring any change in said skin model system.

The skin model system of this invention may also be used for treating patients suffering from a wound to the skin, for example, burn patients. The skin model system may be applied to the wound, for example, by transplantation or grafting.

This invention is further illustrated by the following examples, which are provided for purposes of illustration only. These examples are not intended to limit the scope of this invention.

EXAMPLE 1

Collagen Matrix Formation

Three-dimensional collagenous matrices were prepared from collagen (Devro, Inc.; microcut) which was isolated from the corium layer of the bovine hide by shredding and washing in various solvents in order to obtain a slurry of insoluble collagen particles in water.

See, for example, U.S. Pat. No. 4,703,108, U.S. Pat. No. 4,970,298 and Jain, M. K., et al., "Material Properties of Living Soft Tissue Composites," *J. Biomed. Mat. Res.*, 22:311–326 (1988), the disclosures of which are herein incorporated by reference. Since collagen swells when exposed to acid, the slurry was prepared by adding 6 gm collagen to 100 ml 0.001N Hcl, Ph 3, and allowed to swell. The slurry was then blended to produce a smooth dispersion. (In some preparations, 30 mg polylysine were added per 100 ml of dispersion corresponding to 0.5% polylysine per collagen wt/wt, as described below in Example 2.) The dispersion of collagen in acid (250 ml) was then poured into molds of teflon lined pans 8" by 8" to a depth of 3–4 millimeters. The molds had flat bottoms and were open to the air on top. The dispersions were frozen at −20° C. and lyophilized to form a matrix. The matrix was then crosslinked using a dehydrothermal treatment (110° C. in a vacuum of less than 10 m torr). The collagen matrices were cut with a cork borer to a diameter of 1.5 cm or with a razor blade to squares of approximately 2 cm by 2 cm. The matrices were sealed in plastic and sterilized with gamma irradiation using 2.5 m rad of $^{60}$Co (Isomedix, Inc.) and stored in a dry state (FIG. 1).

The pore structure of the matrices produced by freezing and lyophilizing varied from approximately 50 to 200$\mu$. The pore structure at the surface of the matrix was more open for the air side of the matrix and more closed for the side of the matrix in contact with the mold.

EXAMPLE 2

Preparation of Modified Collagen Matrices

In attempt to change the surface charge on the matrices to improve cell attachment and growth, matrices were modified by the incorporation of 0.5% wt per wt polylysine or polyaspartic acid per collagen. The polylysine or polyaspartic acid was added to the collagen in the acid dispersion for incorporation into the sponge prior to pouring into the mold and freeze drying. In order to determine if the surface charge was changed, the matrices were examined by measuring their streaming potential. Streaming potentials of matrices were measured with a horizontal streaming potential chamber. See Walsh, W. R., et al., "Electrokinetic Effects on Matrix Fibroblast Interactions," *BRAGS* (1992). The electrical potentials in 0.145M, pH 7.3, sodium veronal buffer were measured using silver/silver chloride electrodes and a Keithley 642 Electrometer and x-t recorder. Collagen sponges were equilibrated in the streaming potential chamber for 30 minutes followed by 5 minutes at a flow rate of 1 ml/min. Streaming potentials at several flow rates, corresponding to different pressures, were determined after 30 seconds of flow at a given pressure when the signal was stable as indicated on x-t recorder. The slope of the flow rate versus streaming potential is inversely related to the zeta potential. The zeta potential is defined as the average potential difference between the bulk solution, considered to be zero potential, and the surface of shear (near the matrix).

Figure 2:
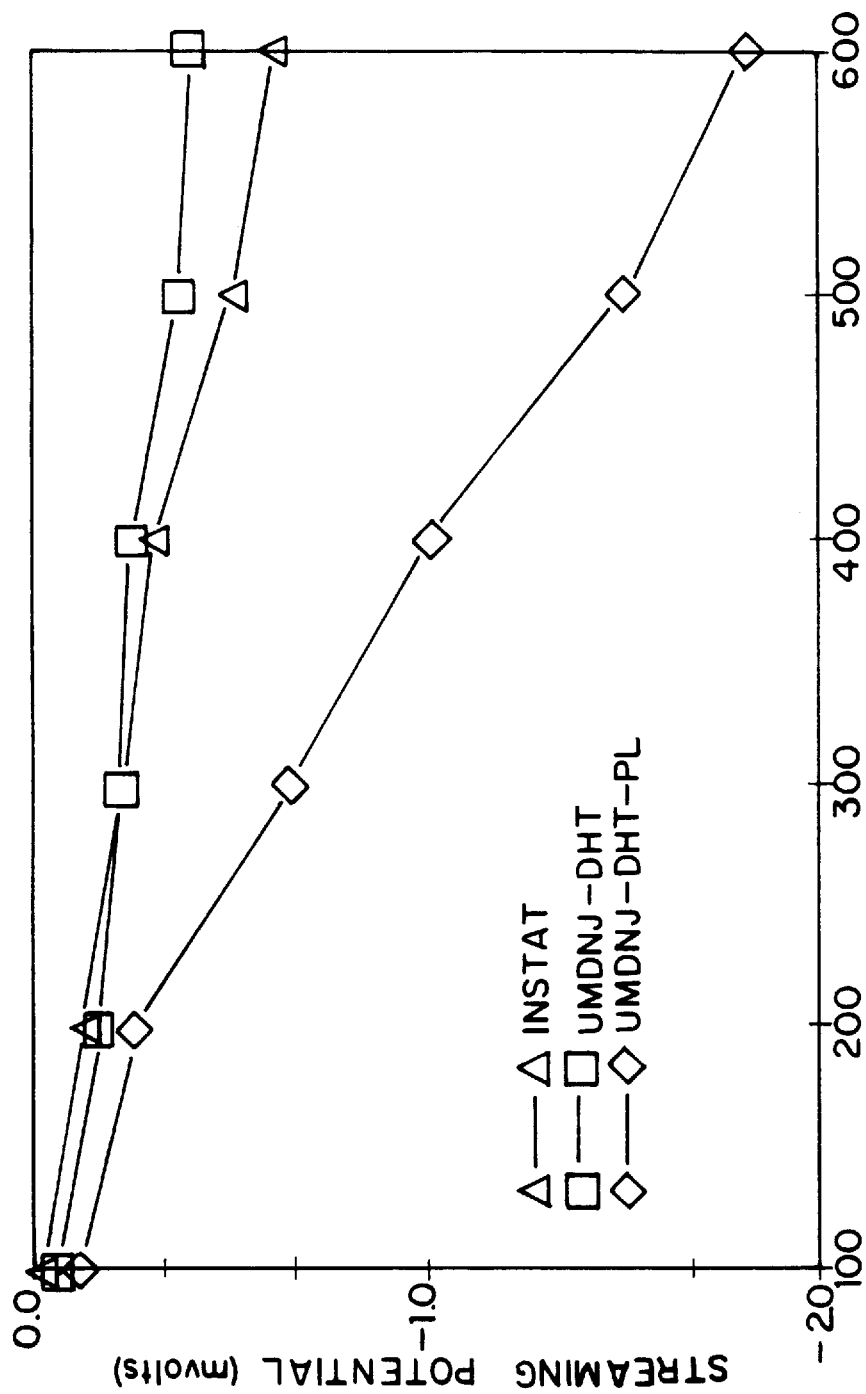
FIG. 2 is a graph of the streaming potential versus flow rate for matrices of this invention not containing polylysine (UMDNJ-DHT), matrices of this invention containing polylysine (UMDNJ-DHT-PL), and a commercially available collagen hemostatic sponge (INSTAT).

Results are presented in FIG. 2 as a graph of the screaming potential versus flow rate for the matrix of this invention not containing polylysine (UMDNJ-DHT), matrices of this invention containing polylysine (UMDNJ-DHT-PL), and a commercially available collagen hemostatic sponge (INSTAT) (INSTAT™ sponges are a product of Johnson & Johnson Co.) The streaming potentials for all collagen matrices tested were negative at pH 7.3 in 0.145M buffer. Since the slope of the flow rate versus streaming potential is inversely related to the zeta potential with the electrode polarity used in the streaming potential chamber, the matrices all had positive zeta potentials. The zeta potential was positive for the matrices without polylysine and more positive for the polylysine matrices (FIG. 2). The streaming potential increased as the flow rate increased (applied pressure increased), as predicted by electrokinetic theory. (Lyklema, J., et al., *J. Colloid Sci.*, 16:501–512 (1961).

EXAMPLE 3
Cell Attachment and Growth Curve Assays in Collagen Matrices

Primary cultures of newborn human dermal fibroblasts (American Type culture Collection) were seeded at a density of 1,2, or $3 \times 10^5$ cells per well on 24-well flat bottom tissue culture plates either with or without matrices (0.9 cm diameter) and grown for 4 hrs in Dulbeccos's modified eagle's medium (DMEM) supplemented with 10% fetal bovine serum, penicillin (100 units/ml), streptomycin (100 /g/ml), 0.1 mM nonessential amino acids and 2 mM 1-glutamine to determine cell attachment. Cells were incubated at 37° C. with 5% $CO_2$ in dishes with and without matrices. To measure cell growth with time, $3 \times 10^5$ cells were seeded per well and cultured for up to one week. Cell density was determined for three plates per condition at the various times using the MTT assay (See Mosmann, T., *J. of Immunological Methods*, 65:55–63 (1983)) Briefly, matrices were removed from the culture dishes prior to assaying. MTT (3-(4,5-dimethylthiazol-2-yl)-2,5-diphenyl tetrazolium bromide) was dissolved in phosphate-buffered saline (PBS) at 5 mg/ml and filter sterilized. Media of all wells to be assayed were replaced with 1 ml fresh media. An aliquot of 100 μl stock MTT solution was added to each well. The plates were incubated at 37° C. for 4 hours. After incubation, 1 ml acid-isopropanol (0.04N HCl in isopropanol) was added to each well. The solution was mixed by vortexing vigorously and the optical density at 570 nm wavelength was measured using a spectrophotometer.

In general, fibroblasts seeded onto the collagen matrix attached more poorly and proliferated more slowly than when seeded on plastic culture dishes. However, those cells which were grown on matrices crosslinked using the dehydrothermal technique allowed cell attachment and growth at levels which approached those produced on tissue culture dishes alone. Preliminary experiments have demonstrated that the doubling time for fibroblasts grown on collagen matrices is increased from 18 hrs to 50 hrs compared with fibroblasts grown on plastic (not shown). Similar results have been reported for fibroblasts contained within LSE's prepared from soluble collagen. In the case of LSE's, after the gels undergo contraction, fibroblast proliferation was reduced to a steady late which was slower than that seen for cells grown on culture dishes. When human dermal fibroblasts were seeded onto sponges at a density of 300,000 per well of 24 well plates, cell growth was similar for cells grown on the fibrillar collagen matrix compared with plastic. Cell growth on a hemostatic sponge (INSTAT) was lower than on plastic, and cell number decreased with time. The decrease in cell number may have been due to cell detachment, cell death or cell migration off of the sponge. The exact cause was not determined here.

Since fibroblasts proliferated slowly on the three-dimensional matrix, the number of fibroblasts introduced during the seeding had to be increased in order to provide sufficient fibroblasts to form a dermis to support epidermal cell growth. Seeding at a concentration of $2.5 \times 10^5$ cells/cm$^2$ of matrix has been found to provide sufficient fibroblasts.

The presence of polylysine changed the surface charge of the matrix, improved the growth of fibroblasts and improved the ability of the matrices to support epidermal cell growth and differentiation.

EXAMPLE 4
Growth of Fibroblasts for in-vitro SMS production

Matrices were soaked overnight in DMEM supplemented with 10% calf serum to remove residual acid. They were then seeded with $0.2-1 \times 10^6$ human dermal fibroblasts per 2×2 cm sponge in the same media. Fibroblasts were cultured on the matrix for 7 days, and transferred to sterile petri dishes and seeded with human epidermal cells as described below.

EXAMPLE 5
Preparation of Comparative Living Skin Equivalents LSE)

For purposes of comparison, LSE's were prepared according to the method of Bell et al. See, Bell, E. B., et al., "Production of a tissue-like structure by contraction of collagen lattices by human fibroblasts of different proliferative potential in vitro," *Proc. Natl. Acad. Sci. USA*, 76:1274–1278 (1979). Primary human dermal fibroblasts were suspended in DMEM containing 10% calf serum at $1.0–1.4 \times 10^5$ cells/ml. One ml of cell suspension and 2 ml of the same culture medium were added to 1 ml of rat tail collagen (Type I; collaborative Research, Inc.) at a concentration of 2.5 mg/ml in 10 mM acetic acid. The cell suspension-collagen solution was poured into a 35 mm petri dish and incubated in a 37° C. tissue culture incubator in 5% $CO_2$ for 5 days to allow contraction to occur.

EXAMPLE 6
Effect of Matrix on Attachment and Growth of Cells

To determine the effect of different constructions and components of collagen matrices on the ability of cells to attached to the matrix, cells were applied to plastic tissue culture plates alone (PLASTIC) and to different collagen matrices as follows:

INSTAT—a commercially available collagen sponge

INSTAT-C commercially available collagen sponge crosslinked with cyanamide (crosslinked by treatment with 1% solution of cyanamide in neutral pH)

UMDNJ-C—collagen matrix of this invention crosslinked with cyanamide (crosslinked by treatment with 1% solution of cyanamide in neutral pH)

Figure 3:
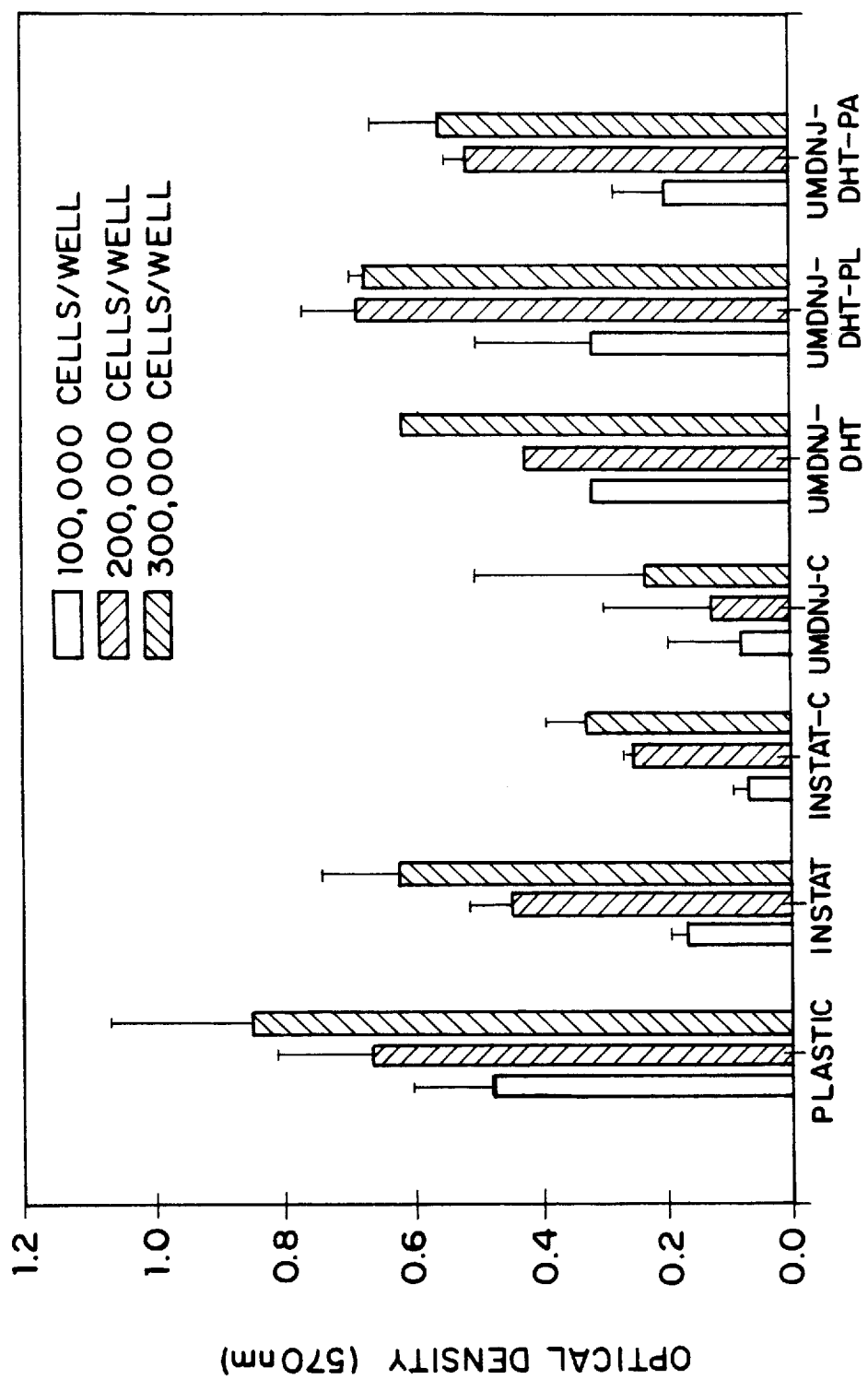
FIG. 3 is a graph of optical density of cell cultures on several different matrices, evidencing the ability of dermal fibroblasts to attach to these matrices. PLASTIC is polylysine-coated plastic tissue culture dish; INSTAT is a commercially available collagen sponge; INSTAT-C is a commercially available collagen sponge crosslinked with cyanamide; UMDNJ-C is a collagen matrix of this invention crosslinked with cyanamide; UMDNJ-DHT is a collagen matrix of this invention crosslinked by dehydrothermal treatment; UMDNJ-DHT-PL is a collagen matrix of this invention crosslinked by dehydrothermal treatment and incorporating polylysine; UMDNJ-DHT-PA is a collagen matrix of this invention crosslinked by dehydrothermal treatment and incorporating polyaspartic acid. Cell density was determined by the MTT assay as described in the examples.

UMDNJ-DHT—collagen matrix of this invention crosslinked by dehydrothermal treatment UMDNJ-DHT-PL—collagen matrix of this invention crosslinked by dehydrothermal treatment and incorporating polylysine UMDNJ-DHT-PA—collagen matrix of this invention crosslinked by dehydrothermal treatment and incorporating polyaspartic acid The cultures were assayed four hours later for cell density. The ability of dermal fibroblasts to attach to these matrices is shown in FIG. 3.

Cyanamide crosslinking of collagen matrices inhibited the attachment of fibroblasts to either a commercially available collagen sponge (INSTAT-C) or the matrix produced here (UMDNJ-C). Those matrices which were crosslinked using a dehydrothermal technique (UMDNJ-DHT) permitted cell attachment at levels which were closer to that seen with plastic tissue culture plates alone (PLASTIC). The addition of polylysine to the matrix (UMDNJ-DHT-PL) had perhaps a slight enhancement of cell attachment while polyaspartic acid (UMDNJ-DHT-PA) had no effect.

Figure 4:
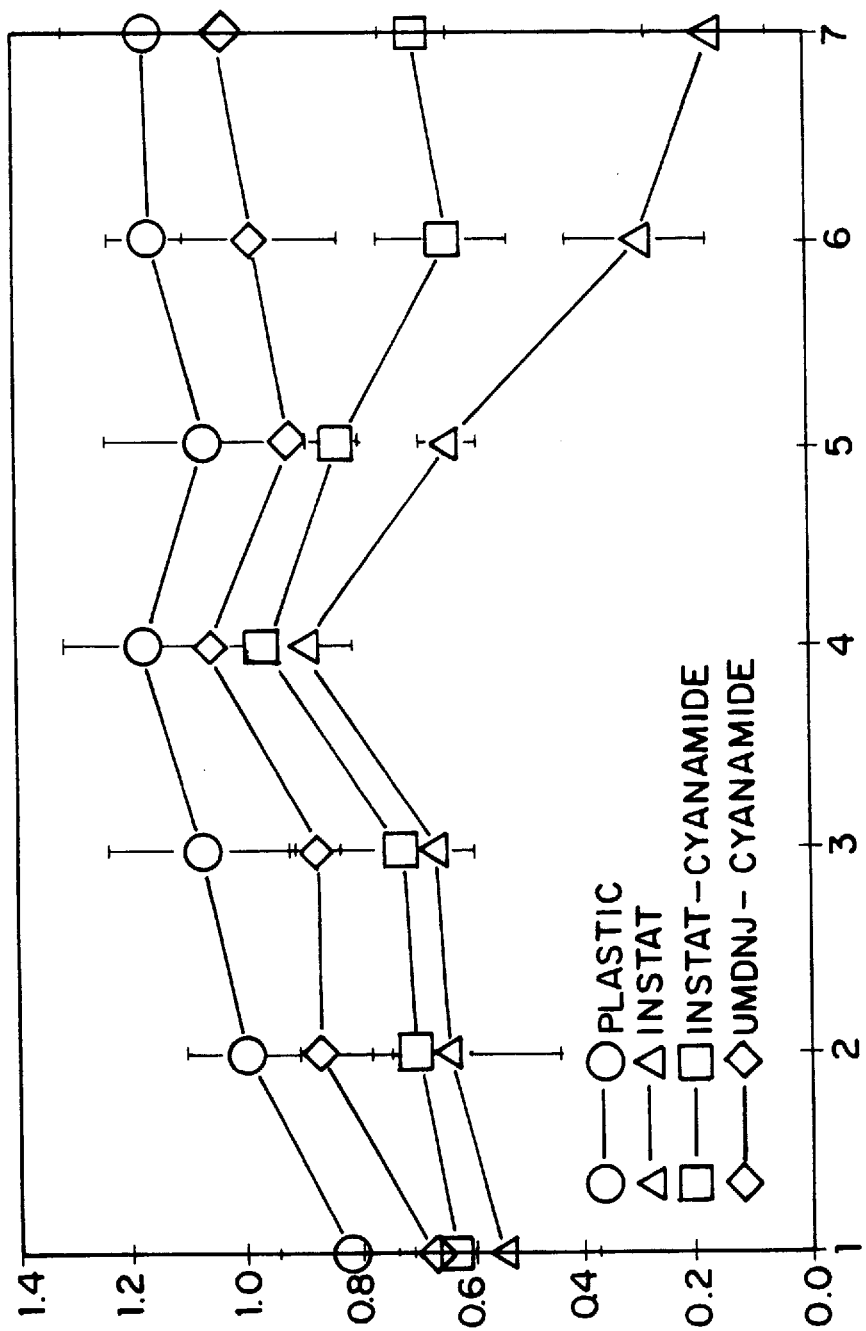
FIG. 4 is a graph illustrating the ability of cells to grow on plastic tissue culture dishes (PLASTIC) compared to their ability to grow on a commercially available collagen sponge (INSTAT), a cyanamide crosslinked version of the same matrix (INSTAT-CYANAMIDE), and a cyanamide crosslinked version of the matrix described here (UMDNJ-CYANAMIDE).

To further analyze the ability of a collagen matrix to influence the growth of cultured cells, fibroblasts were grown on collagen matrices for 1–7 days and assayed for cell density at various points along this time course. In FIG. 4, the ability of cells to grow on plastic tissue culture dishes (PLASTIC) is compared to their ability to grow on the same commercially available collagen sponge (INSTAT), a cyanamide crosslinked version of the same matrix (INSTAT-CYANAMIDE), and a cyanamide crosslinked version of the matrix described here (UMDNJ-CYANAMIDE). All of the matrices tested in this experiment demonstrated reduced cell densities compared to tissue culture plastic; however, the UMDNJ matrix permitted better cell growth than the commercial collagen sponge. Interestingly, although cyanamide crosslinking was shown to inhibit cell attachment, it was shown here to enhance cell growth (compare INSTAT to INSTAT-CYANAMIDE).

Figure 5:
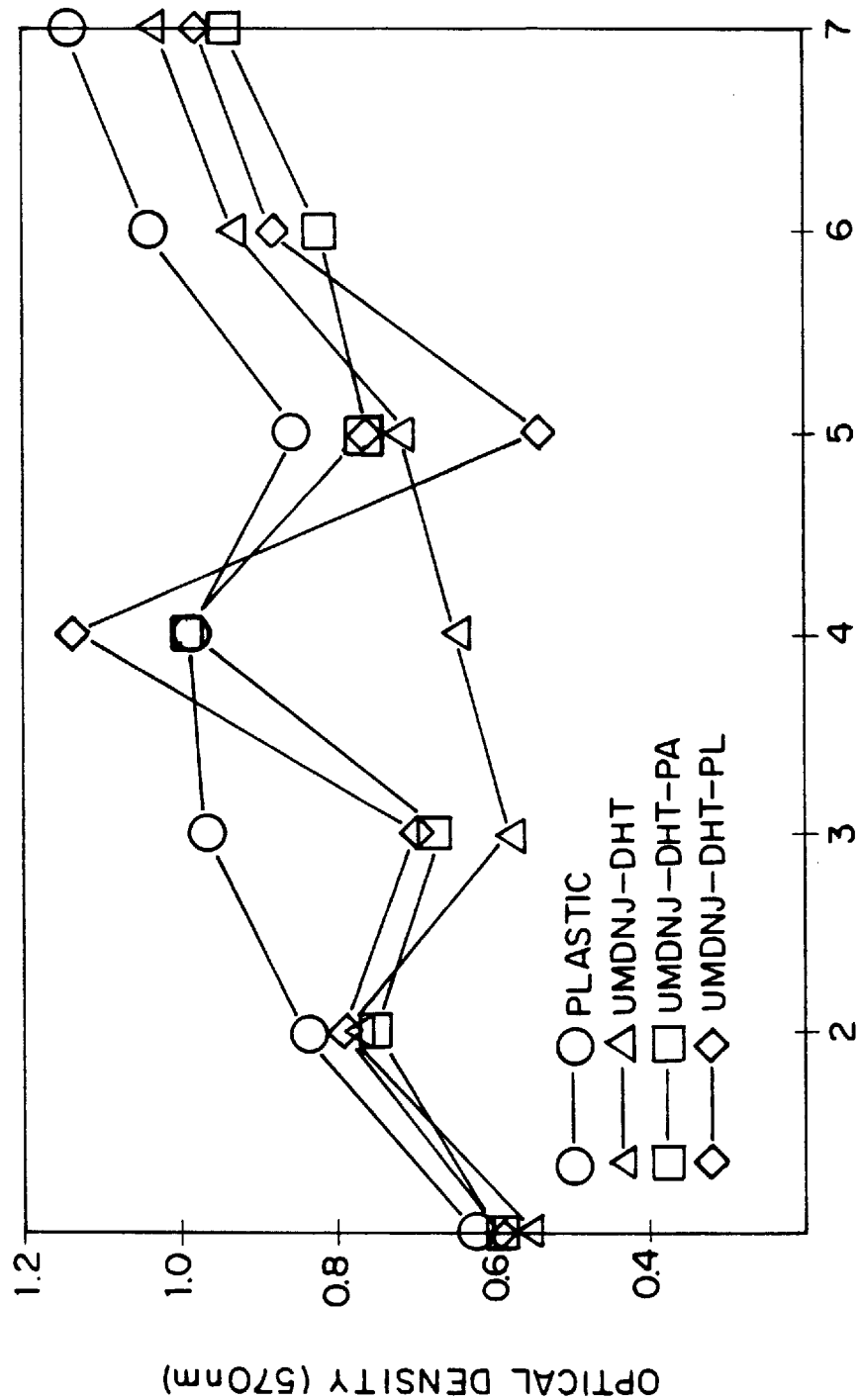
FIG. 5 is a graph showing the effect of added polyamino acids on cell growth in collagen matrices. 3× cells were incubated either on tissue culture dishes (PLASTIC) or with one of several collagen matrices: the matrix described here crosslinked by a dehydrothermal technique (UMDNJ-DHT), the same matrix with polylysine (UMDNJ-DHT-PL), or polyaspartic acid (UMDNJ-DHT-PA) incorporated during its manufacture. Cell density was determined by the MTT assay described in the examples.

The effect of added polyamino acids on cell growth in collagen matrices is shown in FIG. 5. No dramatic effect on cell growth was seen with the incorporation of either polylysine (UMDNJ-DHT-PL) or polyaspartic acid to matrices crosslinked by the dehydrothermal technique (UMDNJ-DHT). However all of the matrices which were crosslinked by the dehydrothermal technique, either with or without additional molecules, performed nearly as well as cells grown on plastic culture dishes (PLASTIC) alone.

EXAMPLE 7

Keratinocyte Cultures

Human keratinocytes were obtained from foreskin (Clonetics Corporation) and grown for five days in Keratinocyte Basal Medium (KBM) supplemented with Epidermal Growth Factor (EGF), insulin, hydrocortisone and Bovine Pituitary Extract (all from Clonetics) according to the procedure described in Clonetica Technical Bulletin. Prior to use, the culture media were switched to an epidermal growth media (E-media) containing 3:1 of high-glucose version of DMEM supplemented with Ham's F-12 Nutrient Mixture (Gibco), followed by the addition of $5 \times 10^{-10}$M cholera toxin (Schwarz-Mann Biotech). In addition, 2 µg/ml hydrocortisone, 25 µg/ml insulin, 25 µg/ml transferrin, and $1 \times 10^{-10}$M triiodothyronine (all from Sigma Chem. Co.) were added to prepare E-media.

EXAMPLE 8

Addition of Keratinocytes to Dermal Matrices

After fibroblast culture of five to seven days, $1.0 \times 10^6$ keratinocytes were added to the surface of the collagen matrix of Example 4 and to the surface of the LSE of Example 5. The resulting cultures were grown at 37° C. and 7% $CO_2$, submerged in E-media. Cultures remained submerged for approximately one week to allow for epidermal attachment and monolayer formation. At this time they were placed on a steel mesh grid at the liquid-air interface. Cultures were then fed every other day with E-media. The dermal matrices were harvested 21 days (except where noted) after raising the culture to the liquid/air interface. The tissues were frozen in liquid nitrogen until they were sectioned.

Figure 6A:
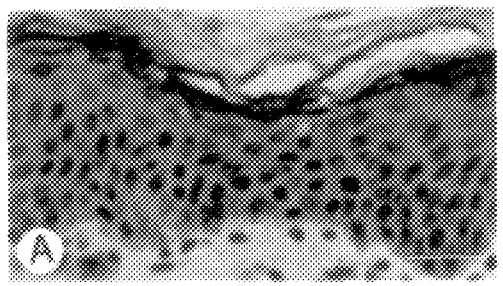
FIG. 6A shows human foreskin.

The skin model systems of this invention (based on collagen matrices as prepared in Example 1) were examined by light microscopy and compared to human neonatal foreskin. (FIG. 6) In normal skin (FIG. 6A), a dermal layer consisting of connective tissue and fibroblasts was apparent over which was a stratified epidermal layer containing keratinocytes of varying degrees of differentiation. The layers include a stratum basalis, spinosum, granulosum and corneum. When keratinocytes were cultured on the Bell skin equivalent for 10 days (FIG. 6B), stratified layers similar to those seen in foreskin were evident. In the stratum corneum-like layer, nucleated cells persisted unlike that which occurs in normal skin. Also evident was the lack of vasculature in the dermal-like layer which also contained fewer fibroblasts compared with skin. With longer term cultures (up to 21 days), these stratified layers persisted (FIG. 6C) although the stratum corneum appeared hyperkeratinized.

Figure 6B:
FIG. 6B shows the Bell skin equivalent after ten days of culturing.
Figure 6C:
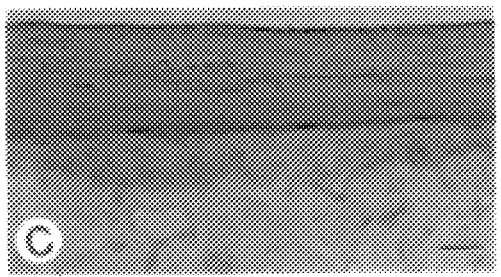
FIG. 6C shows the same after 21 days of culture.
Figure 6D:
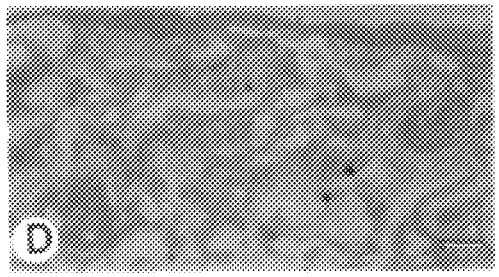
FIG. 6D shows keratinocytes seeded on the "air side" of a cross-linked matrix of insoluble collagen (no polylysine or polyaspartic acid).
Figure 6E:
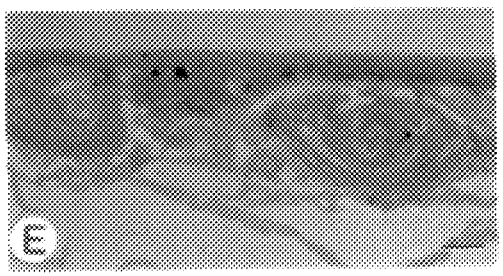
FIGS. 6E and 6F show the skin model system of this invention in which the matrix has been modified with polylysine.
Figure 6F:
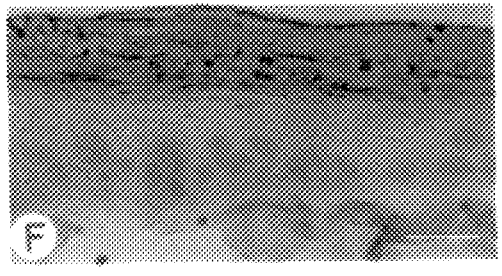

When the keratinocytes were seeded and cultured on the air side of cross-linked, insoluble collagen matrices (unmodified by polylysine), no distinct layers were formed (FIG. 6D). Epidermal cells grew across the surface of the matrix and within open spaces which were exposed to the surface. Within these spaces were pockets of epidermal cells which grew in whorls in the interior of the matrix. These epidermal cells were differentiated in some respects as was evident by immunostaining (data not shown).

With the incorporation of polylysine into the matrices and the addition of keratinocytes to the pan side of the matrix only, most sections showed only one surface layer of epidermal cells, although there were also pockets of epidermal cells near the surface of the matrix (FIG. 6E) seen in some of the outermost regions of the tissue only. Most areas of the matrices demonstrated morphologically distinct layers (FIG. 6F) as shown in the Bell skin equivalents (FIG. 6B). The stratum corneum-like layer produced by epidermal cells cultured on the collagen matrices containing polylysine was parakeratotic as was also demonstrated for epidermal cells cultured on skin equivalents.

EXAMPLE 9

Immunohistochemical Localization

In order to evaluate the level of differentiation of keratinocytes, both culture systems were examined using antibodies to involucrin, a cell envelope protein present in all but the basal layers of normal skin and one of the earlier proteins produced for the formation of the corneocyte envelope in human skin; filaggrin, a protein produced in the suprabasal layer as profilaggrin and processed to filaggrin; keratin K1 which is present in the most highly differentiated keratinocytes; and loricrin, a major cornified envelope precursor, one of the latest envelope proteins to be expressed in normal skin.

Tissues were embedded in Histo Prep embedding compound (Fisher Scientific). Four micron sections of both foreskin and epidermal cultures were cut from frozen tissue on a cryostat (Minotome Corp.) and mounted on gelatin coated slides, air dried, and fixed in acetone (−20° C.) for five minutes. Sections were stained by standard indirect immunochemical techniques. See, for example, Vadesande, F., et al., "Peroxidase-antiperoxidase Techniques," in *Methods in the Neurosciences*, (Cuello, A. C., ed.), John Wiley & Sons: Chichester, Pa. 3:101–120 (1983).

The primary antibodies used were: mouse monoclonal anti-human filaggrin (Biomedical Technologies, Inc.) and rabbit anti-human involucrin (see Simon, M. A., et al., "Involucrin in the epidermal cells of subprimates," *J. Invest. Dermatol.*, 92:721–724 (1989)), rabbit anti-mouse K1 (see Rosenthal, D. S., et al., "A human epidermal differentiation-specific keratin gene is regulated by calcium but not negative modulators of differentiation in transgenic mouse keratinocytes," *Cell Growth and Different.*, 2:107–113 (1991)), or rabbit anti-mouse loricrin (see Hohl, D., et al., *J. Biol. Chem.*, 2666626–6636 (1991)).

Control sections were incubated with the appropriate nonimmune antiserum. Those sections visualized by immunofluorescence were hydratad in PBS (phosphate buffered saline) followed by sequential incubation in 12% BSA (Sigma Chemical Co.) in 0.01M Tris-buffered saline (TBS), normal blocking serum, primary antibody, and finally the fluorescein-conjugated secondary antibody (Sigma Chemical Co.). For immunoenzyme staining, the procedure was similar except the last incubation was replaced by a sequential incubation in biotinylated secondary antibody (Vector) followed by the avidin-biotin-peroxidase complex (Vector). Antibody binding was then visualized using 3,3'-diaminobenzidine (Sigma Chemical Co.). The sections were then counterstained in Hematoxylin (Sigma Chemical Co.) and mounted. All incubations were done in a humidity chamber.

Involucrin—The presence of involucrin was shown, by staining, in all but the basal layers of the skin. Staining of the LSE (per Examples 5 and 7) produced stained positive for involucrin in all suprabasal layers. When the skin model system (SMS) of this invention was examined, similar suprabasal staining was seen throughout the epidermis, however, light staining was seen in the basal layer. Some nonspecific dermal staining of the collagen matrices was noted in both culture models. Sections incubated in nonimmune serum as a control showed no staining of either collagen matrix model.

Filaggrin—Filaggrin is found in human skin in the upper stratum spinosum and granulosum. Generally, staining of the stratum corneum does not indicate the presence of filaggrin, possibly because filaggrin is degraded to amino acids in that layer. In LSE, the stratum granulosum and spinosum-like layers stained positively with no staining seen in the stratum corneum-like layer. Similar distribution of staining was seen in the SMS developed here when stained for filaggrin. Control sections incubated with non-immune serum showed no staining.

Keratin K1—In normal skin, K1 staining was localized to the upper stratum spinosum and granular layers. In the SMS developed here, a staining pattern similar to that of foreskin was seen. With the LSE, light staining was present in a distribution similar to that of foreskin and the skin model system. Some staining was also seen in the stratum corneum. Background dermal staining was present in both the skin model system and foreskin. Sections incubated with nonimmune immunoglobulin as a control showed no staining.

Loricrin—When using an antibody specific to the epitopes on the N-terminal portion of loricrin, foreskin stained specifically from the upper stratum spinosum to the stratum corneum. When LSE cultures were stained with antibodies to loricrin, similar results were obtained With the skin model system of this invention, a lighter but consistent staining pattern was seen when compared to tissue equivalents. A similar pattern of staining and difference in intensity between models was seen with an antibody directed at the C-terminal portion of loricin. Non-immune serum controls showed no staining.

The foregoing examples demonstrate the ability of a crosslinked collagen matrix to serve as a substrate for the assembly of an in vitro skin model system which compares favorably to the model produced by the methods of Bell et al. and normal skin. This model possesses a number of attributes which represent potential advantages over currently available technologies of this kind. The skin model system of this invention is less expensive to manufacture than the living skin equivalent utilizing soluble collagen and living cells. Since the base collagen matrix is made without living cells, it is possible to modify the matrix or to covalently or noncovalently incorporate additional components into the matrix by a process which could be detrimental to living cells (e.g., the dehydrothermal crosslinking step). The collagen matrix of the skin model system of this invention can be stored in its lyophilized state. In contrast, the collagen matrix of the living skin equivalent contains living cells and must be maintained under special conditions. The skin model system of this invention can be made in a wide variety of shapes and sizes and is noncontracting under normal conditions. The collagen/cell matrix of the LSE contracts as the cells proliferate, making it difficult to produce a sheet to the desired size and shape.

What is claimed is:

1. A method of determining the effect of a chemical or agent on human skin comprising contacting a skin model system with said chemical or agent and measuring the interaction of said skin model system and said chemical or agent, wherein:

said skin model system comprises a three-dimensional, cross-linked, porous matrix of insoluble collagen containing fibroblast cells therein, and stratified layers of differentiated epidermal cells supported thereon, wherein a layer of said differentiated epidermal cells is in direct contact with a surface of said three-dimensional, cross-linked, porous matrix of insoluble collagen;

said interaction of said skin model system and said chemical or agent is selected from the group consisting of release of one or more substances by cells of said skin model system, an effect on metabolism of cells of said skin model system, an effect on proliferation of cells of said skin model system, an effect on differentiation of cells of said skin model system, and an effect on reorganization of cells of said skin model system; and the extent of such interaction is an indication of the effect of said chemical or agent on human skin.

2. A method for determining the efficacy of a treatment for a skin condition comprising (a) providing a skin model system that comprises a three-dimensional, cross-linked, porous matrix of insoluble collagen containing fibroblast cells therein, and stratified layers of differentiated epidermal cells supported thereon, wherein a layer of said differentiated epidermal cells is in direct contact with a surface of said three-dimensional, cross-linked, porous matrix of insoluble collagen, wherein cells are diseased cells typical of said condition (b) exposing said skin model system to said treatment, and monitoring an effect of said treatment on said skin model system, said effect on said skin model system and said chemical or agent is selected from the group consisting of release of one or more substances by cells of said skin model system, an effect on metabolism of cells of said skin model system, an effect on proliferation of cells of said skin model system, an effect on differentiation of cells of said skin model system, and an effect on reorganization of cells of said skin model system.

3. The method of claim 2 wherein said epidermal cells comprise keratinoctyes.

4. The method of claim 2 wherein said fibroblasts are dermal fibroblasts.

5. The method of claim 2 wherein said collagen matrix has been cross-linked by a dehydrothermal method.

6. The method of claim 2 which is in the form of a sheet having a thickness of in the range of about 1 to 5 mm.

7. The method of claim 1 wherein the effect of a chemical on human skin is determined comprising contacting said skin model system with a chemical.

8. The method of claim 1 wherein the effect of an agent on human skin is determined comprising contacting said skin model system with an agent selected from the group consisting of:

a substance, light and heat.

9. The method of claim 1 wherein said epidermal cells comprise keratinoctyes.

10. The method of claim 1 wherein said fibroblasts are dermal fibroblasts.

11. The method of claim 1 wherein said collagen matrix has been cross-linked by a dehydrothermal method.

12. The method of claim 1 which is in the form of a sheet having a thickness of in the range of about 1 to 5 mm.

* * * * *

UNITED STATES PATENT AND TRADEMARK OFFICE
CERTIFICATE OF CORRECTION

PATENT NO. : 5,888,248
DATED : March 30, 1999
INVENTOR(S) : Richard A. Berg et al It is certified that error appears in the above-indentified patent and that said Letters Patent is hereby corrected as shown below:

Col. 2, line 21, "cheese" should be --these--.

Col. 14, line 3, after "obtained" insert a period --.--

Signed and Sealed this

Thirty-first Day of August, 1999

Attest:

Q. TODD DICKINSON

Attesting Officer

Acting Commissioner of Patents and Trademarks